(12) United States Patent
Friedman et al.

(10) Patent No.: US 7,678,059 B2
(45) Date of Patent: Mar. 16, 2010

(54) NON-INVASIVE BLOOD PRESSURE MONITOR WITH IMPROVED PERFORMANCE

(75) Inventors: Bruce A. Friedman, Tampa, FL (US); Sai Kolluri, Tampa, FL (US); Lawrence T. Hersh, Tampa, FL (US)

(73) Assignee: General Electric Company, Schenectady, NY (US)

( * ) Notice: Subject to any disclaimer, the term of this patent is extended or adjusted under 35 U.S.C. 154(b) by 518 days.

(21) Appl. No.: 11/248,099

(22) Filed: Oct. 12, 2005

(65) Prior Publication Data

US 2007/0106163 A1    May 10, 2007

(51) Int. Cl.
  *A61B 5/02* (2006.01)
(52) U.S. Cl. ..................... 600/485
(58) Field of Classification Search .............. 600/485, 600/493, 494, 496
  See application file for complete search history.

(56) References Cited

U.S. PATENT DOCUMENTS

| | | | | |
|---|---|---|---|---|
| 4,290,434 A * | 9/1981 | Jewett | ........... | 600/493 |
| 4,543,962 A | 10/1985 | Medero et al. | | |
| 4,638,810 A | 1/1987 | Ramsey, III et al. | | |
| 4,873,987 A | 10/1989 | Djordjevich et al. | | |
| 4,926,873 A * | 5/1990 | Frankenreiter | ........... | 600/494 |
| 5,052,397 A | 10/1991 | Ramsey, III et al. | | |
| 5,237,997 A * | 8/1993 | Greubel et al. | ........... | 600/485 |
| 5,303,711 A * | 4/1994 | Sciarra | ........... | 600/493 |
| 5,579,776 A | 12/1996 | Medero | | |
| 5,649,543 A | 7/1997 | Hosaka et al. | | |
| 5,785,659 A | 7/1998 | Caro et al. | | |
| 5,865,756 A * | 2/1999 | Peel, III | ........... | 600/490 |
| 6,186,953 B1 | 2/2001 | Narimatsu | | |
| 6,358,213 B1 | 3/2002 | Friedman et al. | | |
| 6,648,828 B2 | 11/2003 | Friedman et al. | | |
| 2001/0012916 A1* | 8/2001 | Deuter | ........... | 600/485 |
| 2004/0077959 A1* | 4/2004 | Narimatsu | ........... | 600/490 |
| 2004/0171943 A1* | 9/2004 | Hersh et al. | ........... | 600/490 |
| 2004/0181157 A1* | 9/2004 | Medero et al. | ........... | 600/500 |
| 2005/0148885 A1* | 7/2005 | Tweed et al. | ........... | 600/490 |
| 2005/0251059 A1* | 11/2005 | Kim | ........... | 600/513 |

* cited by examiner

*Primary Examiner*—Charles A Marmor, II
*Assistant Examiner*—Christian Y Jang
(74) *Attorney, Agent, or Firm*—Andrus, Sceales, Starke & Sawall, LLP

(57) ABSTRACT

A blood pressure measurement system that utilizes both a non-invasive blood pressure (NIBP) monitor having a blood pressure cuff and a continuous non-invasive blood pressure (CNIBP) monitor. During operation of the NIBP monitor, the blood pressure cuff is inflated to an initial inflation pressure greater than the systolic blood pressure for the patient being monitored. The CNIBP monitor calculates an estimated blood pressure that is supplied to the NIBP monitor. The NIBP monitor utilizes the continuous, estimated blood pressure to select a target inflation pressure for the blood pressure cuff. During operation of the NIBP monitor, the size of the pressure steps from the initial inflation pressure to a final pressure can be varied based upon the continuous blood pressure estimate from the NIBP monitor.

12 Claims, 7 Drawing Sheets

NON-INVASIVE BLOOD PRESSURE MONITOR WITH IMPROVED PERFORMANCE

BACKGROUND OF THE INVENTION

The present invention relates to an automated blood pressure measuring apparatus and method. More specifically, the present invention relates to an automated non-invasive blood pressure (NIBP) monitor that utilizes a continuous non-invasive blood pressure (CNIBP) monitor to enhance the performance of the NIBP monitor.

Automated blood pressure monitoring has rapidly become an accepted and, in many cases, essential aspect of human treatment. Such monitors are now a conventional part of the patient environment in emergency rooms, intensive and critical care units, and in the operating theater.

The oscillometric method of measuring blood pressure involves applying an inflatable cuff around an extremity of a patient's body, such as a patient's upper arm. The cuff is inflated to a pressure above the patient's systolic pressure and then the cuff pressure is reduced either continuously or incrementally in a series of small steps. A pressure sensor measures the cuff pressure, including the pressure fluctuations resulting from the beat-to-beat pressure changes in the artery under the cuff. The data from the pressure sensor is used to compute the patient's systolic pressure, mean arterial pressure (MAP) and diastolic pressure An example of the oscillometric method of measuring blood pressure is shown and described in U.S. Pat. Nos. 4,360,029; 4,394,034; and 4,638,810, which are commonly assigned with the present invention.

Although NIBP methods, such as the oscillometric method described above, are effective in determining the blood pressure of a patient, it is frequently desired to be able to measure the blood pressure on a continuous basis, such as with a hospitalized patient. One technique of providing a continuously measured blood pressure is to insert a saline filled catheter through a patient's vascular system to the point at which the blood pressure measurements are desired. The catheter is connected to a pressure sensor, which measures the pressure in the vessel. As an alternative method, the catheter, rather than being fluid filled, could have a pressure sensor at the tip that directly senses the blood.

Although these catheter techniques have proven effective and continuously monitor a patient's blood pressure, both involve making an incision into the patient's skin for insertion of the catheter into the blood vessel. As a consequence, this invasive procedure entails some risk of complication to the patient and is in most cases undesirable.

Although several methods currently exist for providing a continuous, non-invasive blood pressure estimate, various factors can affect the accuracy of such measurements. For example, changes in the physiological state of the patient can bring about changes in the arterial wall elasticity. In general, changes in the arterial wall elasticity will affect the measured pulse wave velocity. If the elastic modulus of the arterial wall changes, the relationship between arterial pressure and arterial distension also changes. If the operating point obtained using a blood pressure cuff calibration is used, then any changes in the arterial elasticity will require re-calibration and, if no re-calibration is performed, errors in the pressure estimation can clearly occur.

U.S. Pat. No. 6,648,828, commonly assigned with the present application and incorporated herein by reference, teaches a method that utilizes pulse wave velocity to create a continuous, non-invasive blood pressure measurement. The '828 patent teaches a method of measuring the pulse wave velocity within a patient and a method of relating such pulse transit time to blood pressure. Although the '828 patent teaches a method of accurately measuring the PWV, the relationship of PWV to blood pressure can often be difficult to achieve.

Thus, although various CNIBP monitoring systems and methods currently exist, these systems provide a somewhat unreliable estimate and have not yet replaced NIBP monitoring systems.

During the use of a conventional NIBP monitoring system, the blood pressure cuff is placed around the arm of a patient and is inflated to a pressure that fully occludes the brachial artery to prevent blood flow. The cuff is then progressively deflated and a pressure transducer detects pressure pulses as blood begins to flow past the pressure cuff. As can be understood, the selection of the initial inflation pressure determines the amount of time and deflation required before the NIBP system begins to detect cuff oscillations and blood flow. If the initial inflation pressure is selected well above the systolic blood pressure for the patient, the NIBP system over inflates the blood pressure cuff, resulting in patient discomfort and extended measurement time. Alternatively, if the initial inflation pressure is selected below the systolic blood pressure for the patient, the blood pressure cuff must reinflate to obtain an accurate reading. Therefore, it is desirable to utilize the blood pressure estimate from a CNIBP system to enhance the performance of a NIBP system.

SUMMARY OF THE INVENTION

The following describes a method and apparatus for monitoring the blood pressure in a patient that uses two separate monitoring systems to improve the performance of the blood pressure monitoring. The combined blood pressure monitoring system includes a non-invasive blood pressure (NIBP) monitoring system that includes a blood pressure cuff that can be placed on the patient. The blood pressure cuff is selectively inflated and deflated by a central processor, which controls the availability of pressurized air to the cuff and the position of valves that release air from the cuff. During the deflation of the blood pressure cuff, oscillometric pulses are detected and the processor calculates the blood pressure based upon the recorded oscillometric pulses.

During the initial measurement, the NIBP monitor inflates the blood pressure cuff to a target inflation pressure that is above the systolic pressure for the patient. Preferably, the target inflation pressure is selected only slightly above the systolic pressure to avoid unnecessary over inflation of the blood pressure cuff.

The method and system use a continuous, non-invasive blood pressure (CNIBP) monitor to continuously estimate the blood pressure of the patient and generate a continuous blood pressure estimate. The CNIBP monitor estimates the blood pressure on a continuous basis based upon parameters recorded from the patient. Since the CNIBP monitor generates a continuous estimate of the blood pressure, the CNIBP monitor provides a current estimate of the systolic blood pressure, diastolic blood pressure and mean arterial pressure (MAP) for the patient at any given time.

When the NIBP monitor begins the process of inflating the blood pressure cuff, the central processor of the NIBP monitor utilizes the continuous blood pressure estimate from the CNIBP monitor to select the target inflation pressure. Since the selection of the target inflation pressure is based upon an estimate of the current blood pressure for the patient, the target inflation pressure provides a more accurate estimate of the patient's systolic blood pressure prior to inflation as compared to the NIBP monitoring system alone.

During the determination of the blood pressure for the patient, the NIBP monitoring system decreases the blood pressure cuff inflation pressure in a series of steps from the target inflation pressure to a final inflation pressure. In one embodiment of the invention, the central processor of the NIBP monitoring system intelligently varies the size of each of the pressure steps based upon the continuous blood pressure estimate received from the CNIBP monitor. Since the continuous blood pressure estimate provides current estimates for the systolic blood pressure, MAP and diastolic blood pressure, in a second embodiment of the invention, the central processor can adjust the size of the pressure steps based upon the continuous blood pressure estimate. By varying the size of the pressure steps, the system can provide enhanced measurement resolution near the systolic, diastolic and MAP while providing larger steps to bring the blood pressure cuff inflation pressure down from the systolic pressure to the MAP and from the MAP to diastolic pressure. Thus, the combined blood pressure monitoring system can more effectively and accurately determine the blood pressure and yet operate more quickly as compared to a standard NIBP monitoring system alone.

BRIEF DESCRIPTION OF THE DRAWINGS

The drawings illustrate the best mode presently contemplated of carrying out the invention. In the drawings.

DETAILED DESCRIPTION OF THE PREFERRED EMBODIMENT

Figure 1:
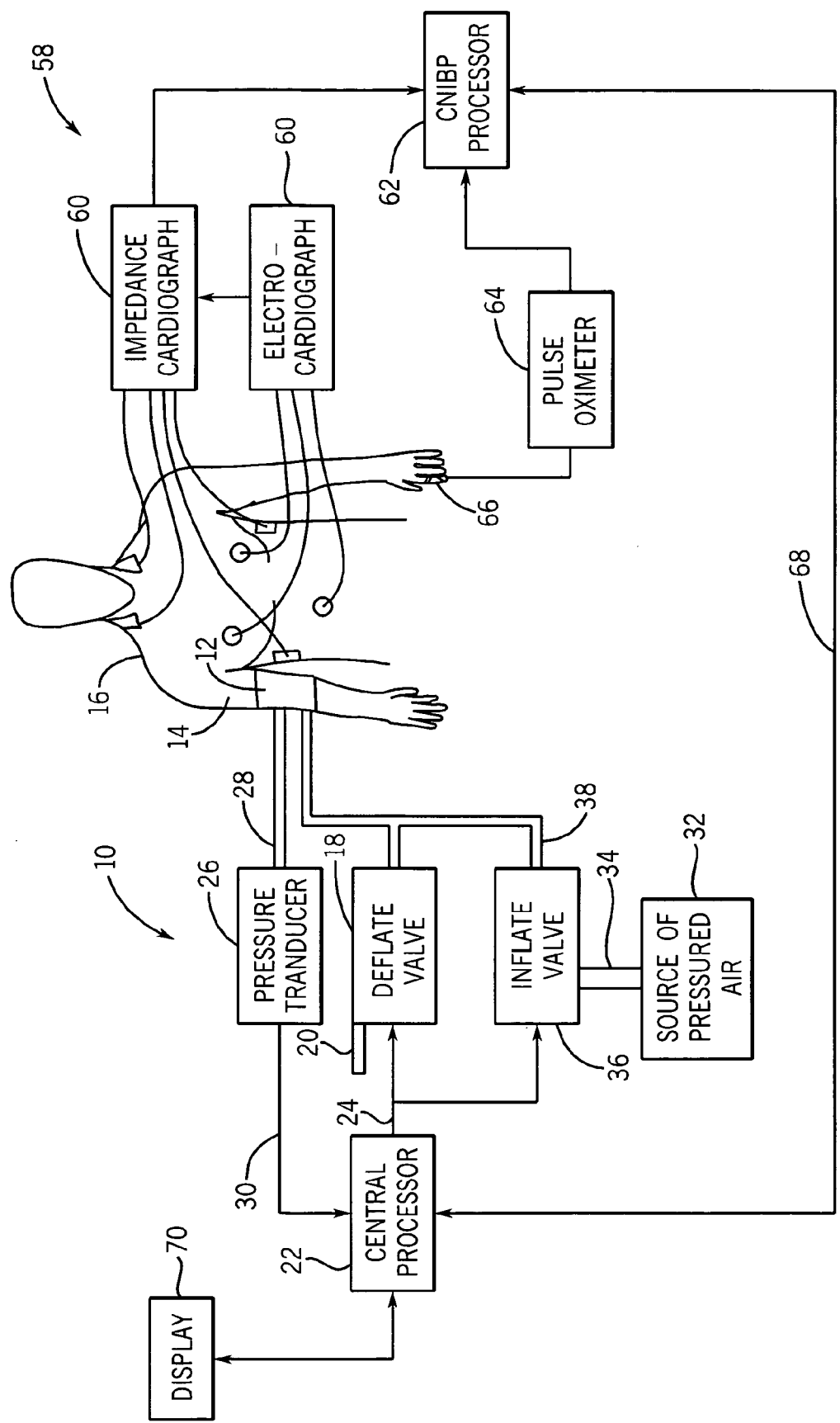
FIG. 1 is a block diagram of a system for monitoring blood pressure in a patient utilizing both a NIBP monitor and a CNIBP monitor.

FIG. 1 generally illustrates a non-invasive blood pressure (NIBP) monitoring system 10 of conventional construction. The NIBP monitoring system 10 includes a blood pressure cuff 12 placed on the arm 14 of a patient 16. The blood pressure cuff 12 can be inflated and deflated for occluding the brachial artery of the patient 16 when in the fully inflated condition. As the blood pressure cuff 12 is deflated using the deflate valve 18 having exhaust 20, the arterial occlusion is gradually relieved. The deflation of the blood pressure cuff 12 by the deflate valve 18 is controlled by a central processor 22 through the control line 24.

A pressure transducer 26 is coupled by duct 28 to the blood pressure cuff 12 for sensing the pressure within the cuff 12. In accordance with conventional oscillometric techniques, the transducer 26 is used to sense pressure oscillations in the cuff 12 that are generated by pressure changes in the brachial artery under the cuff. The electrical signals from the pressure transducer 26 are obtained by the central processor 22, using an analog-to digital converter, through connection line 30.

A source of pressurized air 32 is connected by duct 34 to an inflate valve 36. The inflate valve 36 is connected by duct 38 to the blood pressure cuff 12. The operation of the inflate valve 36 is controlled by the central processor 22 through the control line 24. Thus, the inflation and deflation of the blood pressure cuff 12 is controlled by the central processor 22 through the deflate valve 18 and the inflate valve 36, respectively.

From the standpoint of the principles of the present invention, the processing of the signals from pressure transducer 26 by the central processor 22 to produce blood pressure data, and optionally to reject artifact data, can be conducted in accordance with the prior art teachings of the above-referenced Ramsey '029 and '034 patents. Alternatively, the blood pressure can be determined in accordance with the teachings of Medero et al in U.S. Pat. No. 4,543,962, of Medero in U.S. Pat. No. 4,546,775, of Hood, Jr. et al in U.S. Pat. No. 4,461,266, of Ramsey, III et al in U.S. Pat. No. 4,638,810, of Ramsey III et al in U.S. Pat. No. 4,754,761, of Ramsey III et al in U.S. Pat. No. 5,170,795, of Ramsey III et al in U.S. Pat. No. 5,052,397, of Medero in U.S. Pat. No. 5,577,508 and of Hersh et al in U.S. Pat. No. 5,590,662, all of which are commonly assigned herewith and the disclosures of which are hereby incorporated by reference. In any event, it is desirable to use any of the known techniques to determine the quality of the oscillation complexes received at each cuff pressure so that the blood pressure determination is made using the physiological relevant cuff pressure oscillations from each heart beat and not artifacts.

Figure 2:
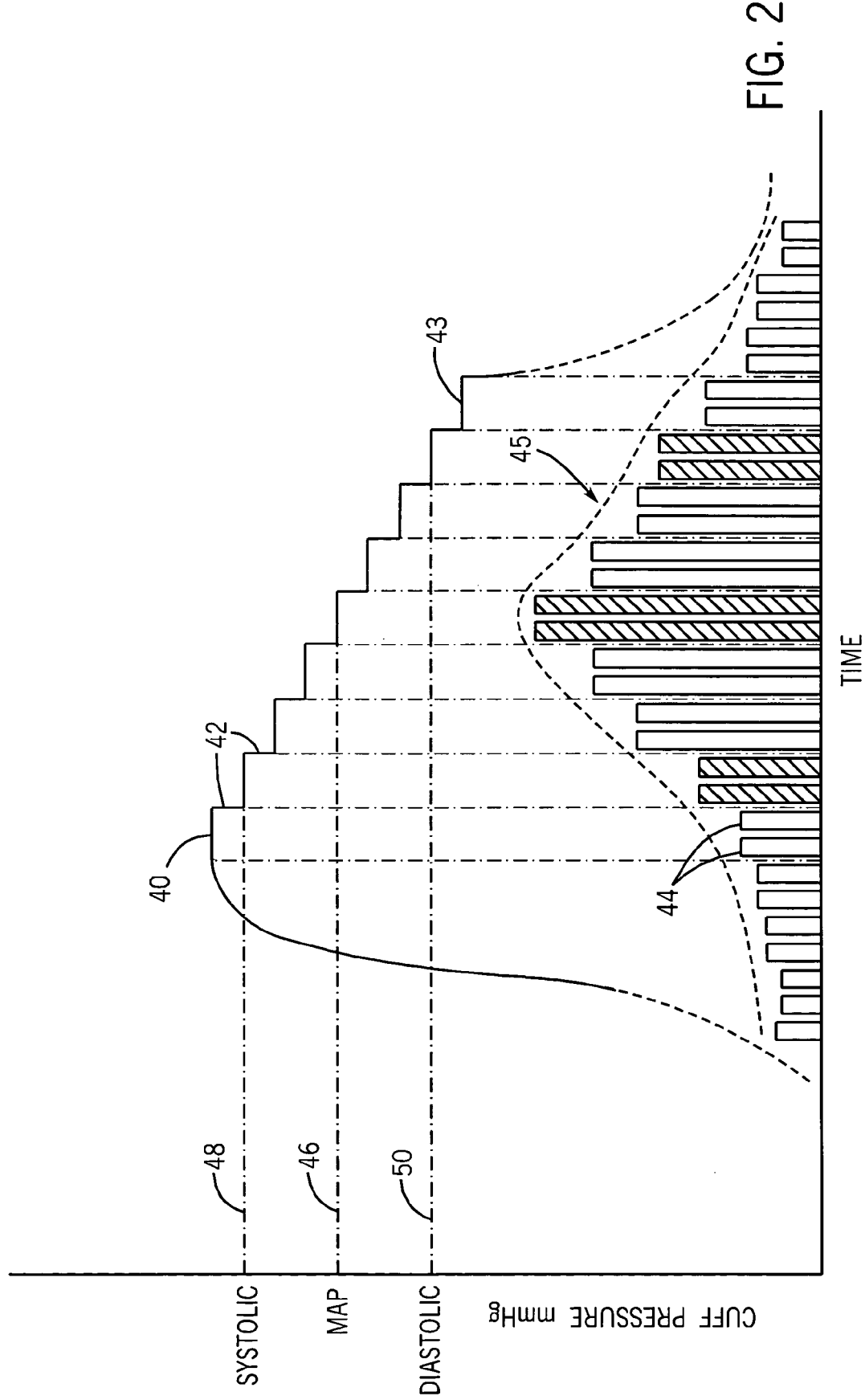
FIG. 2 is a graph depicting the initial cuff inflation pressure relative to the systolic pressure, the mean arterial pressure (MAP) and diastolic pressure.

During normal operation of the NIBP monitoring system 10 shown in FIG. 1, the blood pressure cuff 12 is initially placed on the patient 16, typically around the subject's upper arm 14 over the brachial artery. At the inception of the measuring cycle, the blood pressure cuff 12 is inflated to a pressure that fully occludes the brachial artery, i.e., prevents blood from flowing through the brachial artery at any point in the heart cycle. In FIG. 2, the initial inflation pressure is illustrated by reference number 40.

After the blood pressure cuff has been inflated to the initial inflation pressure 40, the deflate valve is actuated by the central processor to deflate the cuff in a series of pressure steps 42. Although various values for each pressure step 42 can be utilized, in one embodiment of the invention, the pressure step 42 is about 8 mm Hg per step.

After each pressure step 42, the NIBP monitoring system detects and records one or more pressure oscillations 44 for the current cuff pressure level. The pressure transducer measures the internal cuff pressure and provides an analog signal characterizing the blood pressure oscillatory complexes. The peak values of the complex signals are determined within the central processor.

Figure 2A:
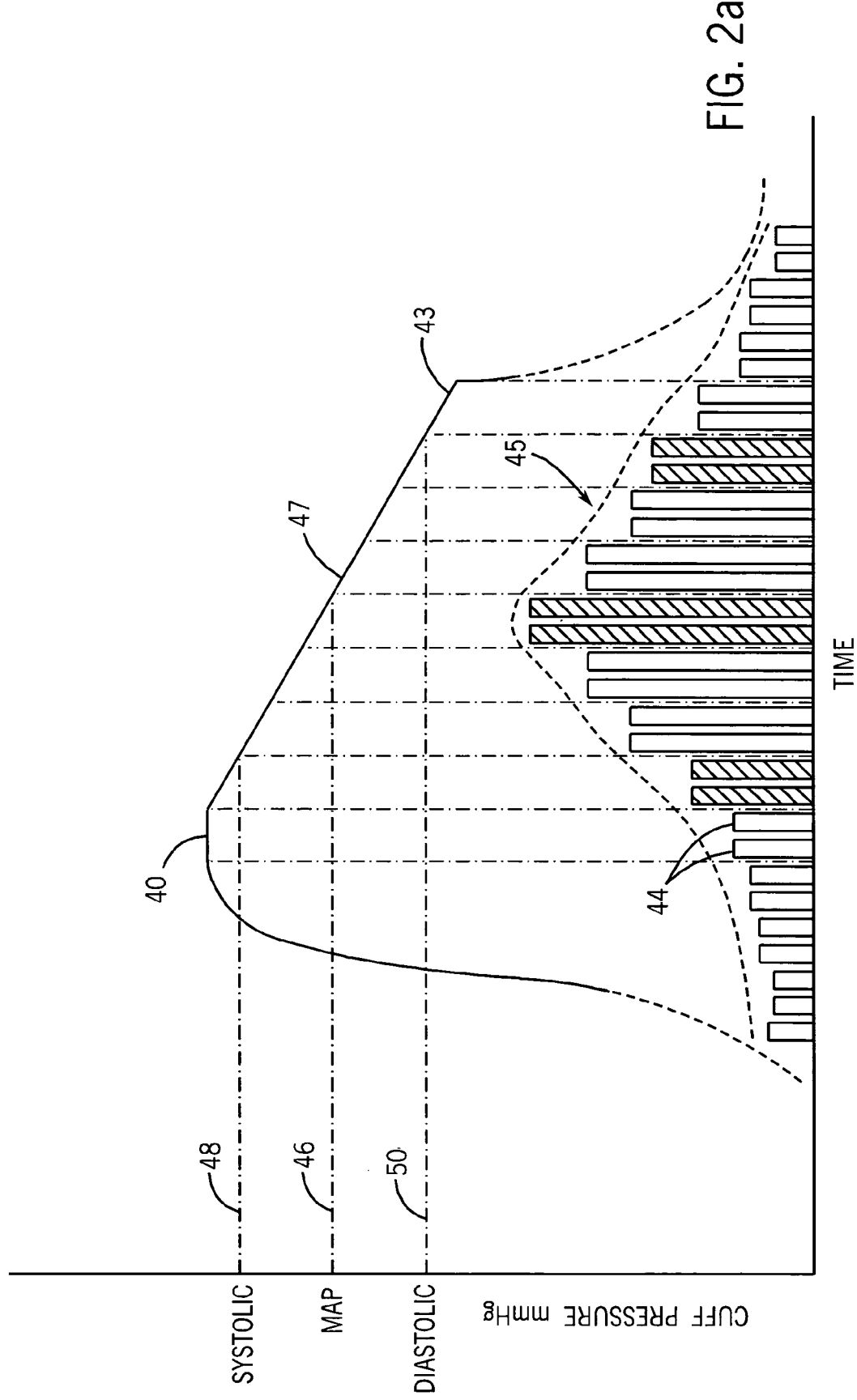
FIG. 2a is a graph similar to FIG. 2 for a NIBP monitor that continuously deflates the blood pressure cuff from the initial cuff inflation pressure to a final pressure.

Although typical cuff pressure control of the NIBP monitoring system is shown in FIG. 2 as including distinct pressure steps 42 from the initial inflation pressure 40 to a final pressure 43, the NIBP monitoring system could also operate with a continuous, smooth, or linear pressure profile from the initial inflation pressure 40 to the final pressure 43, as shown in FIG. 2a. In the embodiment of the NIBP monitoring system shown in FIG. 2a, the central processor continuously decreases the pressure from the initial inflation pressure 40 to the final pressure 43, as shown by the linear section 47 of the graph. As the cuff pressure decreases from the initial inflation pressure, the NIBP monitoring system detects pressure oscillations 44 and records the pressure oscillations for the current cuff pressure. The central processor within the NIBP monitoring system can then calculate the MAP 46, systolic pressure 48 and diastolic pressure 50.

As the measurement cycles progress, the peak amplitude of the blood pressure complexes generally become monotonically larger to a maximum and then become monotonically smaller as the cuff pressure continues toward full deflation, as illustrated by the bell-shaped graph 45 in FIG. 2. The peak amplitude of the cuff pressure oscillation complexes, and the corresponding occluding-cuff pressure values, are retained in the central processor memory. The oscillometric measurements are used by the central processor to calculate the mean arterial pressure (MAP) 46, the systolic pressure 48 and the diastolic pressure 50 in a known manner.

As can be understood in the graph of FIG. 2, the initial inflation pressure 40 for the blood pressure cuff must exceed the systolic pressure 48 for the system and method of the NIBP monitoring to function effectively. In past embodiments of the NIIBP monitoring systems, the initial inflation pressure 40 is based upon the systolic pressure 48 determined during the last measurement cycle. The systolic pressure 48 from the last measurement cycle is typically increased by a set value or percentage to determine the initial inflation pressure 40 for the next measurement cycle. Since the last blood pressure cuff measurement may have been taken at a significant time period before the current measurement, the estimated initial inflation pressure based upon the last measurement may be inaccurate due to changing conditions relative to the patient.

Figure 3:
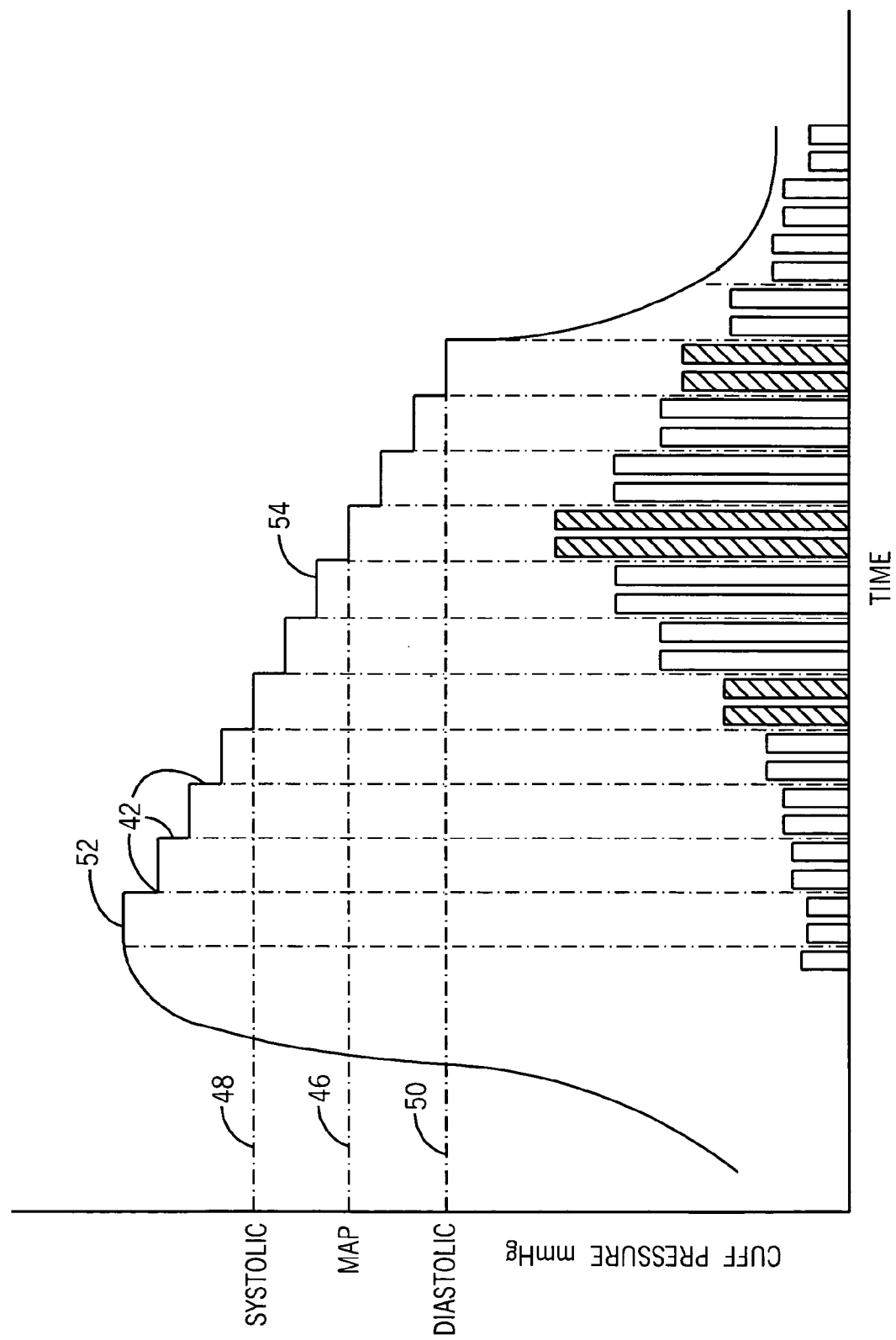
FIG. 3 is a graph illustrating the over inflation of the blood pressure cuff.

Referring now to FIG. 3, thereshown is an example of the operation of the NIBP monitoring system in which the initial inflation pressure 52 is selected significantly higher than the systolic pressure 48. In this operating example, the pressure within the blood pressure cuff must be decreased a significant number of pressure steps 42 before the cuff pressure 54 reaches the systolic pressure 48. The over inflation of the blood pressure cuff results in the patient experiencing discomfort due to unnecessarily high cuff pressures and prolonged occlusion of the brachial artery. Further, the over inflation of the blood pressure cuff increases the overall time required to take a blood pressure reading from the patient due to the numerous pressure steps 42 required before the cuff pressure 54 reaches the systolic pressure 48.

Figure 4:
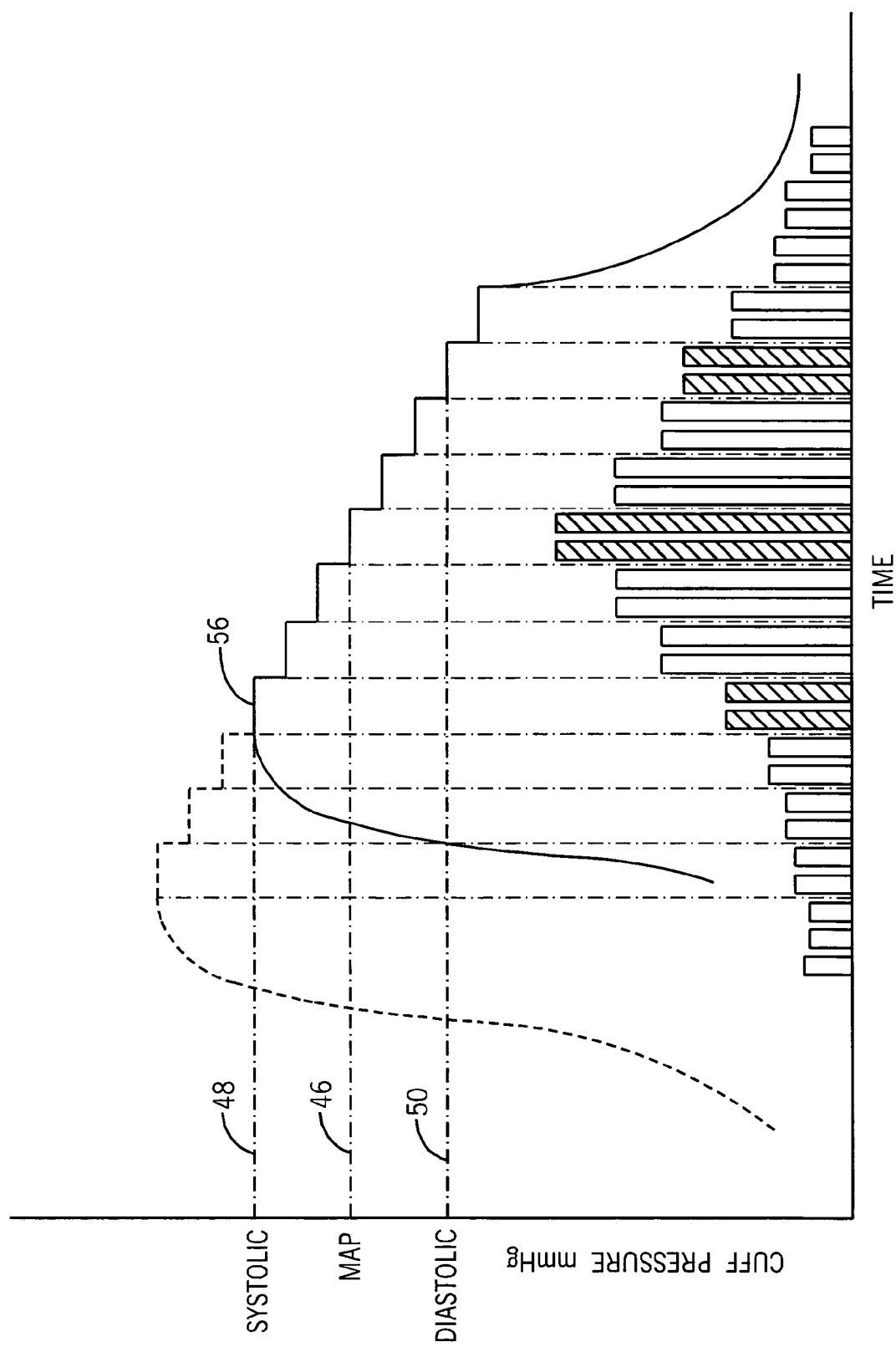
FIG. 4 is a graph illustrating the under inflation of the blood pressure cuff.

In addition to the over inflation, the initial inflation pressure 56 can be incorrectly selected to be below the systolic pressure 48, as shown in FIG. 4. If the initial inflation pressure 56 is below the systolic pressure 48, the NIBP monitoring system will not obtain the required oscillometric pressure measurements needed to accurately calculate the systolic pressure 48. In the situation shown in FIG. 4, the NIBP monitoring system must re-inflate the blood pressure cuff to an inflation pressure that is greater than the systolic pressure 48. In such a situation, the patient again experiences unnecessary reinflation of the cuff, which prolongs the blood pressure determination time and increases patient discomfort.

Although the method of estimating the initial inflation pressure from earlier blood pressure determinations is generally effective, the initial inflation pressure may be in error if the patient's blood pressure has changed significantly in the time between the current NIBP measurement and the previous NIBP determination. In some cases, the amount of time between blood pressure measurements may be 15 minutes to an hour. If the patient's blood pressure has changed significantly in that time period, the standard inflation adjustment may be incorrect and result in either over inflation or under inflation, thereby prolonging the blood pressure determination cycle.

In the system shown in FIG. 1, a continuous, non-invasive blood pressure (CNIBP) monitor 58 is utilized in combination with the NIBP monitoring system 10. The CNIBP monitor 58 shown in FIG. 1 is constructed in accordance with the teachings of U.S. Pat. No. 6,648,828, the disclosure of which is incorporated herein by reference. Although the specifics for the CNIBP monitor 58 are shown and described, it should be understood that various different types of CNIBP monitors 58 could be utilized while operating within the scope of the present invention. Simply, the CNIBP monitor 58 is a system and method coupled to the patient for continuously estimating the blood pressure of the patient, typically through the measurement of other patient parameters.

The illustrative example of a CNIBP monitor 58 includes an impedance cardiograph 60 connected to the patient 16. The impedance cardiograph 60 can determine the thoracic impedance of the patient 16. Changes in the base line thoracic impedance are related to changes in the intravascular and extravascular fluids within the patient's chest. Variations of the thoracic impedance correlate closely with alternations of the central blood volume. This information can be used to identify a point in time at which a pressure pulse emanates from the heart into the vascular system.

As illustrated in FIG. 1, a conventional electrocardiograph 60 produces an output that is used with the input signals from the electrodes of the impedance cardiograph, to allow the impedance cardiograph 60 to calculate the ventricular stroke volume and cardiac output for the patient. These values are supplied to a CNIBP processor 62. The CNIBP processor 62 also receives a signal from a pulse oximeter 64 attached to the index finger of the patient 16 by a conventional probe 66.

In accordance with the method described in U.S. Pat. No. 6,648,828, the CNIBP processor 62 is able to continuously calculate the blood pressure from the pulse transit time. The calculation of the blood pressure estimate by the CNIBP processor 62 includes a determination of the systolic pressure, diastolic pressure and mean arterial pressure. The calculation of the estimated blood pressure for the patient 16 by the CNIBP processor 62 is relayed to the central processor 22 of the NIBP monitoring system 10 through the communication line 68. Upon receipt of the estimated blood pressure from the CNIBP processor 62, the central processor 22 can then selectively display either the blood pressure estimate from the CNIBP processor 62 or the blood pressure measured by the NIBP monitoring system 10, including the blood pressure cuff 12. The blood pressure for the patient 16 is shown on the single display 70.

As described, the central processor 22 continuously receives blood pressure estimates from the CNIBP processor 62. The blood pressure estimates include estimates for the systolic pressure, diastolic pressure and the MAP for the patient.

Figure 5:
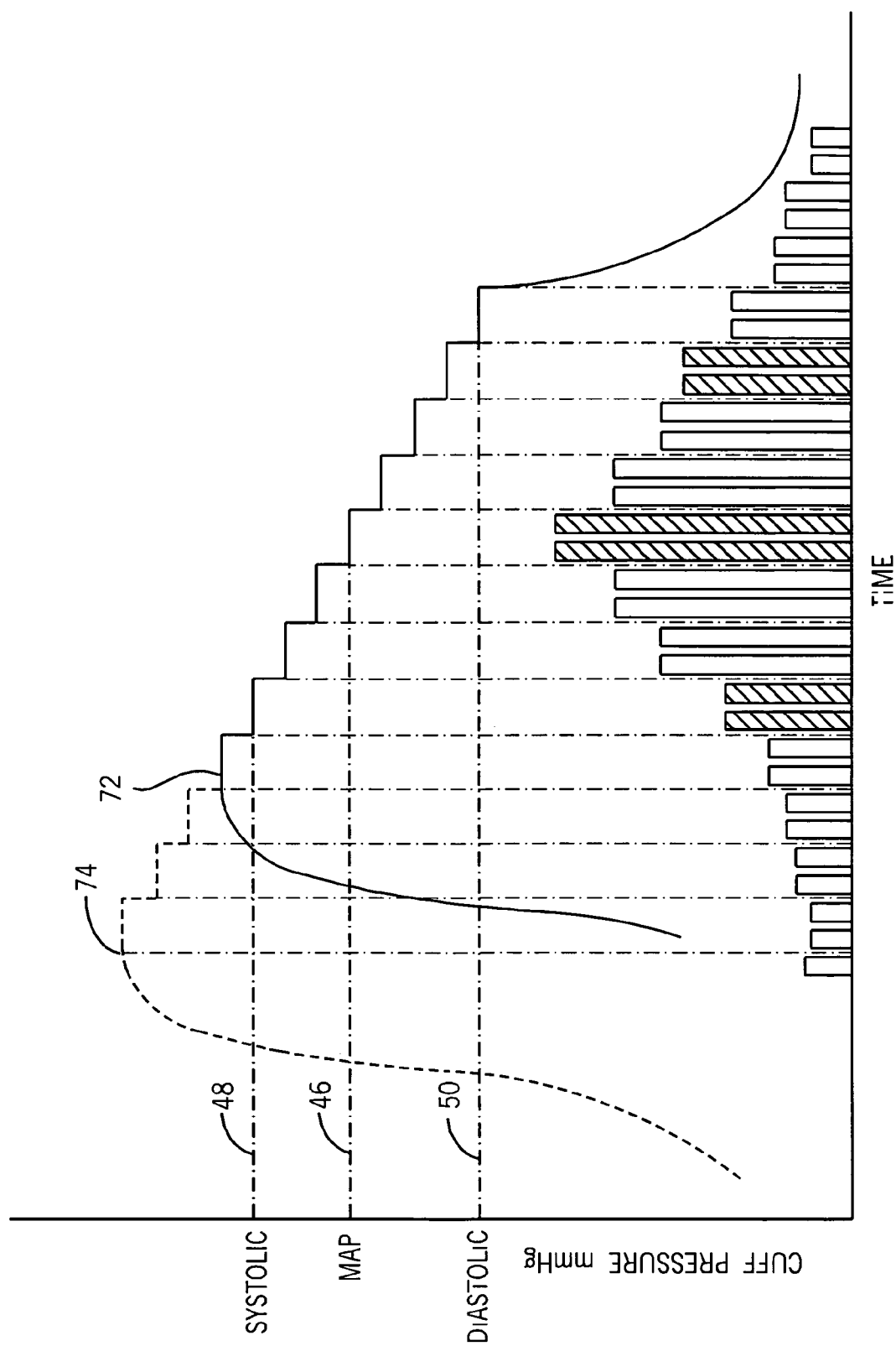
FIG. 5 is a graph illustrating the inflation of the blood pressure cuff to an optimal target pressure.

Referring now to FIG. 5, when the central processor determines another blood pressure measurement must be taken, the central processor can utilize the estimated blood pressure from the CNIBP monitor 58 to select a target inflation pressure 72 and possibly modify the measurement procedure. In the illustration shown in FIG. 5, the initial inflation pressure for the NIBP monitoring system, as calculated using the previous measurement plus an offset value, is shown by reference numeral 74. As illustrated, the initial inflation pressure 74 calculated using the conventional estimating technique is well above the systolic pressure 48 and would thus result in over inflation of the blood pressure cuff and increased determination times. In the embodiment of the invention shown in FIG. 1, the CNIBP processor 62 is continuously generating blood pressure estimates such that the combined system shown in FIG. 1 can use the continuous estimated blood pressure to determine the current systolic pressure and estimate a target inflation pressure. As an example, the target inflation pressure may be determined by the estimated systolic pressure plus some offset to ensure that the target inflation pressure exceeds the systolic pressure. In an alternative embodiment, the target pressure may be determined based on a statistical analysis of the CNIBP data over a previous period. As shown in FIG. 5, the use of the target inflation pressure 72 as calculated by utilizing the CNIBP monitor more closely corresponds to the actual systolic pressure 48 as compared to the initial inflation pressure 74 calculated by the NIBP monitoring system alone.

Figure 6:
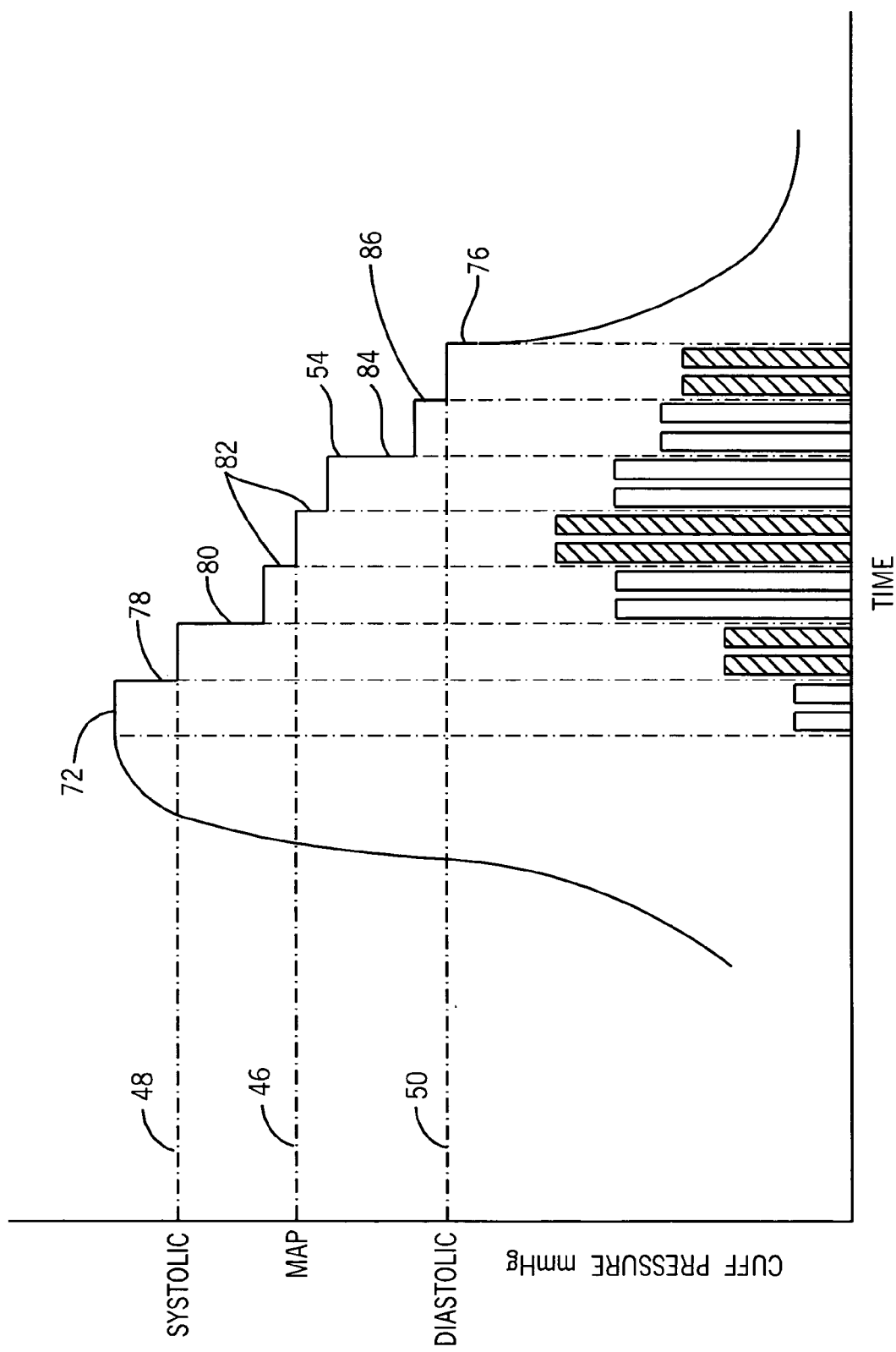
FIG. 6 is a graph illustrating the variable step heights from the optimal target inflation pressure to a final pressure below the diastolic pressure.

Referring now to FIG. 6, in addition to utilizing the estimated blood pressure measurement of the CNIBP monitor 58 to calculate a target inflation pressure, the central processor can also utilize the estimated blood pressure measurements from the CNIBP processor to adjust the size of the pressure steps from the target inflation pressure 72 down to a final pressure 76. As illustrated in FIG. 6, the central processor operates the deflate valve to create a first pressure step 78 to step the cuff pressure 54 down from the target inflation pressure 72. As an example, the first pressure step 78 may have a value of 12 mm Hg as compared to a typical value of 8 mm Hg in the system shown in FIG. 2. The first pressure step 78 steps the cuff pressure 54 to a value close to the systolic pressure 48, as determined from the blood pressure estimates from the CNIBP monitoring system 58. After the oscillations 44 have been measured, the central processor generates a second pressure step 80 to step the cuff pressure 54 down to near the MAP 46 as estimated by the CNIBP monitor 58.

Once the cuff pressure 54 nears the MAP, the central processor creates a series of smaller steps 82 having pressure decrements much smaller than the first pressure step 78 and second step 80. As an example, the smaller steps 82 could be only 6 mm Hg. It should be understood that in the above description, the values given for the first and second pressure steps 78, 80 and the smaller steps 82 are for illustrative purposes only and that the values could be varied depending upon the patient and the pressure control capabilities of the NIBP system. The smaller size of the series of steps 82 allows the system to have increased resolution at pressures near the MAP 46.

Once the central processor detects the rise of the pressure oscillations 44 and the subsequent fall following the MAP 46, the central processor again increases the size of the pressure steps, as indicated by the third pressure step 84. Although only a single third pressure step 84 is shown in FIG. 6, it should be understood that the size of the pressure steps 84 could vary and that multiple steps could be required between the MAP 46 and the diastolic pressure 50.

Once the cuff pressure 54 approaches the diastolic pressure 50, a second series of smaller steps 86 are created by the central processor 22. Once again, at a pressure location near the diastolic pressure 50, the system provides for additional pressure steps to more accurately determine the diastolic pressure 50.

As can be understood by the description of FIG. 6, the central processor can utilize the estimated blood pressure measurements from the CNIBP processor to both set the target inflation pressure 72 and vary the pressure step sizes from the target inflation pressure 72 down to the final pressure 76. In this manner, the system can provide for enhanced measurements near the systolic, MAP and diastolic pressures while increasing the step sizes to allow the cuff pressure 54 to fall more quickly in locations between the systolic pressure and the MAP, as well as the MAP and the diastolic pressure.

A similar methodology could be applied to a monitor using linear deflation by varying the rate of deflation so that an increase in deflation rate corresponds to a larger step Although the blood pressure monitoring system shown in FIG. 1 and including both the NIBP monitoring system 10 and the CNIBP monitor 58 has been described where the NIBP monitoring system 10 is utilized to provide the blood pressure for display by the central processor 22 on the display 70, the system could also be operated in a mode in which the CNIBP monitor 58 is the primary source of blood pressure measurements. During the operation of the CNIBP monitor 58, the CNIBP processor 62 utilizes blood pressure calibration measurements obtained by the NIBP system 10. The blood pressure calibration measurements are utilized by the CNIBP processor 62 to generate continuous blood pressure estimates. When the CNIBP processor 62 determines that additional calibration is required, either based upon expiration of time or through the monitoring of variations in the blood pressure estimates, the CNIBP processor 62 signals the NIBP monitoring system to obtain an actual blood pressure measurement through the blood pressure cuff 12. Since the CNIBP processor 62 is now in communication with the central processor 22 through the communication line 68, the central processor of the NIBP system can utilize the estimated blood pressure from the CNIBP processor 62 to generate a target inflation pressure in the same manner as described above. The use of the estimate blood pressure measurements from the CNIBP processor 62 allows the NIBP monitoring system to more accurately generate a target inflation pressure in the same manner as discussed above. The more accurate estimation of the target inflation pressure further optimizes the operation of the NIBP monitoring system 10 when making a calibration measurement.

Various alternatives and embodiments are contemplated as being within the scope of the following claims particularly pointing out and distinctly claiming the subject matter regarded as the invention.

What is claimed is:

1. A method of monitoring blood pressure in a patient, the method comprising the steps of:
    positioning a blood pressure cuff of a non-invasive blood pressure (NIBP) monitor on the patient;
    providing a continuous, non-invasive blood pressure (CNIBP) monitor operable to continuously estimate the blood pressure of the patient and generate a continuous blood pressure estimate that includes at least an estimated systolic blood pressure;
    calculating a target inflation pressure for the NIBP monitor based upon the continuous blood pressure estimate determined by the CNIBP monitor before inflation of the blood pressure cuff, wherein the target inflation pressure is the estimated systolic blood pressure plus an offset value, wherein the offset value is determined as a statistical function of the estimated systolic pressure over a pre-determined number of the previous beats;
    inflating the blood pressure cuff to the target inflation pressure;
    continuously decreasing the pressure in the blood pressure cuff while monitoring for oscillometric pulses in the blood pressure cuff in the NIBP monitor; and
    calculating the systolic pressure, mean arterial pressure and diastolic pressure based upon the oscillometric pulses detected during deflation of the blood pressure cuff.

2. The method of claim 1 wherein the statistical function of the systolic pressure is the standard deviation.

3. The method of claim 1 wherein the inflation pressure in the blood pressure cuff is decreased from the target inflation pressure to a final pressure through a series of pressure steps, wherein the oscillometric pulses are monitored at each pressure step, wherein each pressure step represents a decrease in the in the cuff pressure.

4. A method of monitoring blood pressure in a patient, the method comprising the steps of:
providing a continuous, non-invasive blood pressure (CNIBP) monitor operable to continuously estimate the blood pressure of the patient and generate a continuous blood pressure estimate;
calculating a target inflation pressure based upon the continuous blood pressure estimate from the CNIBP monitor;
positioning a blood pressure cuff of a non-invasive blood pressure (NIBP) monitor on the patient;
inflating the blood pressure cuff to the target inflation pressure;
decreasing the pressure in the blood pressure cuff from the target inflation pressure to a final pressure through a series of pressure steps;
varying the size of the pressure steps within the series of pressure steps during deflation of the blood pressure cuff between the target inflation pressure and the final pressure, wherein the selection of the size of the pressure steps is based upon the continuous blood pressure estimate to optimize the deflation of the blood pressure cuff;
monitoring for oscillometric pulses in the blood pressure cuff at each pressure step; and
calculating the systolic pressure, mean arterial pressure and diastolic pressure based upon the oscillometric pulses detected during deflation of the blood pressure cuff.

5. The method of claim 4 wherein the CNIBP monitor continuously determines at least an estimate systolic blood pressure, an estimated diastolic blood pressure and an estimate mean arterial pressure, wherein the size of the steps decreases near the mean arterial pressure estimated by the CNIBP monitor.

6. The method of claim 5 wherein the size of the steps are increased between the estimated mean arterial pressure and the estimated diastolic pressure.

7. A method of enhancing the operation of a non-invasive blood pressure (NIBP) monitor having a blood pressure cuff selectively inflatable and deflatable to determine at least a systolic pressure, a mean arterial pressure and a diastolic pressure for a patient, the method comprising the steps of:
providing a continuous non-invasive blood pressure (CNIBP) monitoring system operable to continuously estimate the blood pressure of the patient and generate a continuous blood pressure estimate including at least an estimated systolic blood pressure;
calculating an initial target inflation pressure based upon the continuous blood pressure estimate, wherein the initial target inflation pressure is selected above the estimated systolic blood pressure;
inflating the blood pressure cuff of the NIBP monitor to the initial target inflation pressure, wherein the initial target inflation pressure is calculated based on the continuous blood pressure estimate before inflation of the blood pressure cuff;
deflating the blood pressure cuff from the initial target inflation pressure to a final pressure through a series of pressure steps that each represent a decrease in the inflation pressure in the blood pressure cuff;
varying the size of the pressure steps within the series of pressure steps during deflation of the blood pressure cuff from the initial target inflation pressure to the final pressure, wherein the size of each of the pressure steps of the decreasing pressure values of the blood pressure cuff are based upon the continuous blood pressure estimate;
monitoring for oscillometric pulses in the blood pressure cuff at each of the pressure steps as the blood pressure cuff is deflated from the initial target inflation pressure to the final pressure; and
calculating and displaying the systolic pressure, mean arterial pressure and diastolic pressure based upon the oscillometric pulses.

8. The method of claim 7 wherein the initial target inflation pressure is the estimated systolic blood pressure plus an offset value.

9. The method of claim 7 wherein the CNIBP monitor continuously determines at least an estimate systolic blood pressure, an estimated diastolic blood pressure and an estimate mean arterial pressure, wherein the size of the steps decreases near the mean arterial pressure estimated by the CNIBP monitor.

10. The method of claim 9 wherein the size of the steps are increased between the estimated mean arterial pressure and the estimated diastolic pressure.

11. A system for monitoring blood pressure in a patient, the system comprising:
a central processor;
a non-invasive blood pressure (NIBP) monitor including a pressure transducer coupled to the central processor and operable to detect oscillometric pulses from the patient and a blood pressure cuff positionable on the patient, the blood pressure cuff being coupled to a supply of pressurized air such that the blood pressure cuff can be selectively inflated and deflated by the central processor;
a continuous non-invasive blood pressure (CNIBP) monitor positionable on the patient to continuously estimate the blood pressure of the patient and generate a continuous blood pressure estimate including at least an estimated systolic blood pressure,
wherein in the central processor is operable to inflate the blood pressure cuff to a target pressure and deflate the blood pressure cuff from the target pressure to determine the blood pressure of the patient, wherein the central processor estimates the target pressure based upon the estimated systolic pressure,
wherein the central processor is operable to deflate the blood pressure cuff in a series of pressure steps from the target pressure to a final pressure, wherein the central processor varies the size of the pressure steps within the series of pressure steps during the deflation of the blood pressure cuff from the target pressure to the final pressure, wherein the size of each of the pressure steps is based upon the estimated blood pressure from the CNIBP monitor.

12. The system of claim 11 further comprising a display coupled to the central processor, wherein the central processor displays the detected blood pressure based on the information obtained from the pressure transducer.

* * * * *